US012605440B2

(12) United States Patent
Jung et al.

(10) Patent No.: US 12,605,440 B2
(45) Date of Patent: Apr. 21, 2026

(54) MICRONEEDLE CONTAINING INFLUENZA VACCINE AND INFLUENZA VACCINE PATCH CONTAINING THE SAME

(71) Applicants: UIF (University Industry Foundation), Yonsei University, Seoul (KR); JUVIC INC., Seoul (KR)

(72) Inventors: Hyungil Jung, Seoul (KR); Huisuk Yang, Seoul (KR); Geonwoo Kang, Seoul (KR)

(73) Assignees: UIF (University Industry Foundation), Yonsei University, Seoul (KR); JUVIC INC., Seoul (KR)

( * ) Notice: Subject to any disclaimer, the term of this patent is extended or adjusted under 35 U.S.C. 154(b) by 597 days.

(21) Appl. No.: 18/087,745

(22) Filed: Dec. 22, 2022

(65) Prior Publication Data

US 2023/0414746 A1 Dec. 28, 2023

(30) Foreign Application Priority Data

Jun. 28, 2022 (KR) ........................ 10-2022-0079199

(51) Int. Cl.
| | |
|---|---|
| *A61K 39/145* | (2006.01) |
| *A61K 9/00* | (2006.01) |
| *A61M 37/00* | (2006.01) |
| *A61P 31/16* | (2006.01) |

(52) U.S. Cl.
CPC .......... *A61K 39/145* (2013.01); *A61K 9/0021* (2013.01); *A61M 37/0015* (2013.01); *A61P 31/16* (2018.01); *A61M 2037/0046* (2013.01); *A61M 2037/0061* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 10,265,511 B2 | 4/2019 | McAllister et al. | |
| 2014/0371713 A1* | 12/2014 | Quan | A61M 37/0015 604/173 |
| 2016/0015952 A1* | 1/2016 | Omachi | A61K 9/0021 424/444 |

FOREIGN PATENT DOCUMENTS

EP 3 932 423 A1 1/2022

* cited by examiner

*Primary Examiner* — Shanon A. Foley
*Assistant Examiner* — Myron G Hill
(74) *Attorney, Agent, or Firm* — Knobbe, Martens, Olson & Bear, LLP

(57) ABSTRACT

The present invention relates to a microneedle including an influenza vaccine and particularly a soluble microneedle including an influenza vaccine, and more specifically to a microneedle including an influenza vaccine and an influenza vaccine patch including the same that can increase the stability of the influenza vaccine and expect a higher immune effect by including a water-soluble polymer and an additive at a specific ratio, and when the microneedle including the influenza vaccine of the present invention is used, not only the stability of the vaccine is increased, but also the skin penetration and drug delivery effect are remarkably excellent.

13 Claims, 9 Drawing Sheets

(a)          (b)          (c)

Standard antibody experiment

Low pH experiment

| Viscous solution composition | ELISA (Standard antibody) | ELISA (Low pH) | SRID |
|---|---|---|---|
| 1. PBS+CMC+TRE | 97% | 101% | 108.8% |
| 2. PBS+CMC+ARG | 94% | 96% | 94.0% |
| 3. Phos+CMC+ARG | 81% | 77% | 91.7% |
| 4. Ace+CMC+ARG | 65% | 63% | 78.6% |

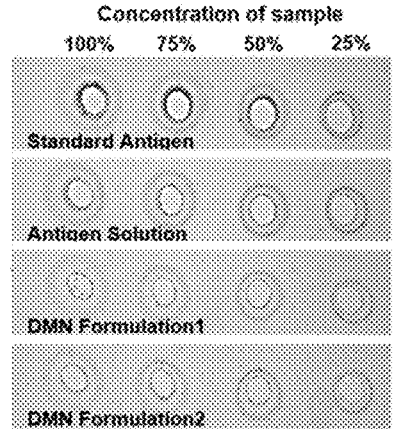

| Sample | Loading antigen | Assay result | Activity |
|---|---|---|---|
| DMN Formulation 1 | 18 μg | 16.8 μg | 93.3% |
| DMN Formulation 2 | 17.4 μg | 15.4 μg | 88.5% |

FIG. 9

| Group | Test material | Boosting | Dose | Route | Challenge | # of animals |
|---|---|---|---|---|---|---|
| 1 | Blank DMN (Negative control) | - | - | ID | | |
| 2 | Injection (Positive control) | X | 15ug/100ul | IM | | |
| 3 | | X | 5ug/patch | ID | | |
| 4 | | O | 5ug/patch | ID | | |
| 5 | Flu-DMN | X | 10ug/patch | ID | 2MLD₅₀ | 5 / group |
| 6 | | O | 10ug/patch | ID | | |
| 7 | | X | 15ug/patch | ID | | |
| 8 | | O | 15ug/patch | ID | | |

※ Loading strain : A/Michigan/45/2015 reassortant virus (H1N1)

Challenge strain : A/Seoul/Y-1/2009 (H1N1)

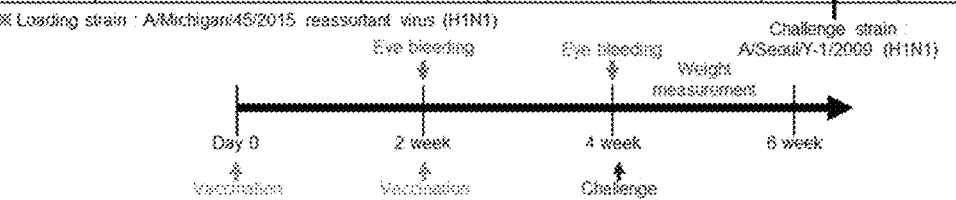

FIG. 10

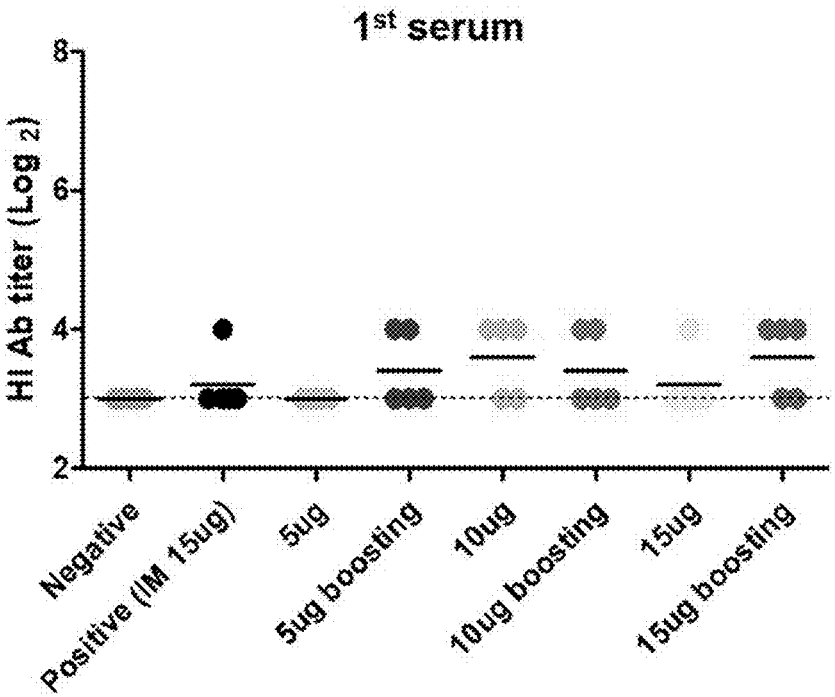
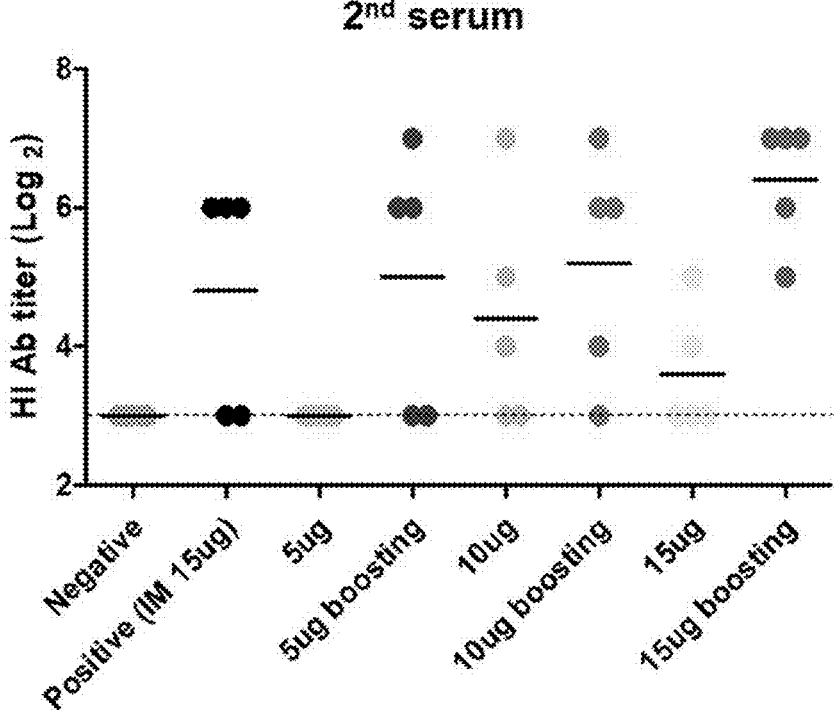
FIG. 11

1st serum
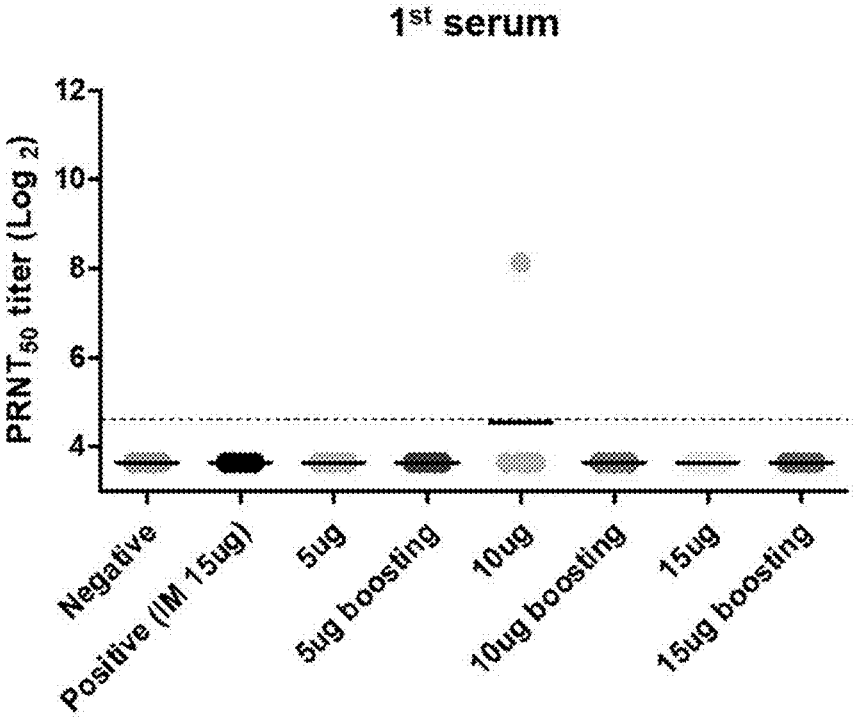
2nd serum
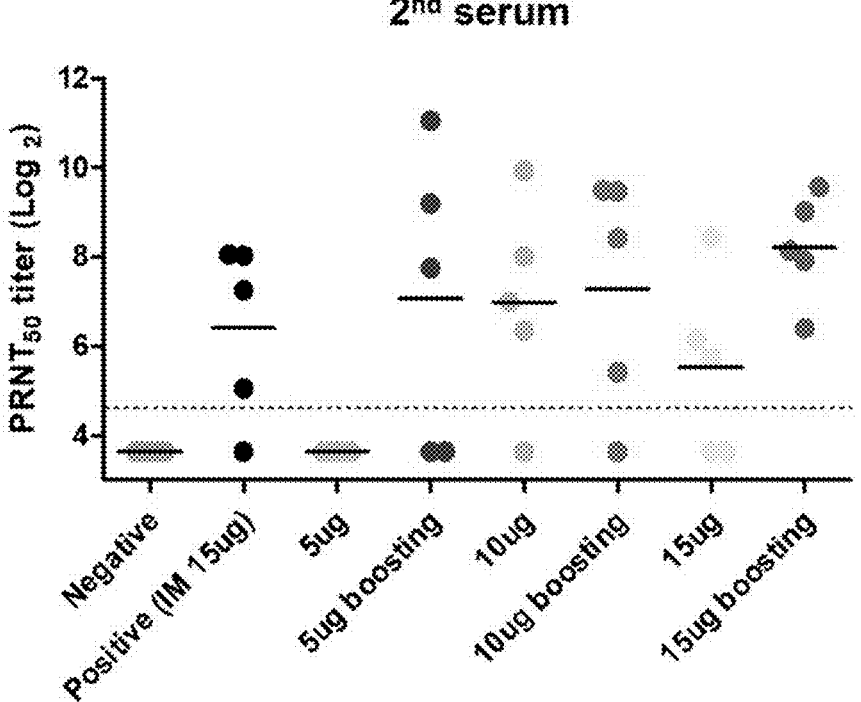
FIG. 12

MICRONEEDLE CONTAINING INFLUENZA VACCINE AND INFLUENZA VACCINE PATCH CONTAINING THE SAME

CROSS-REFERENCE TO RELATED APPLICATION

This application claims priority to and the benefit of Korean Patent Application No. 10-2022-0079199, filed on Jun. 28, 2022, the disclosure of which is incorporated herein by reference in its entirety.

TECHNICAL FIELD

The present invention relates to a microneedle including an influenza vaccine and an influenza vaccine patch including the same, and more specifically to a microneedle including an influenza vaccine and an influenza vaccine patch including the same that can increase the stability of the influenza vaccine and expect a higher immune effect by including a water-soluble polymer and an additive at a specific ratio.

BACKGROUND ART

Numerous drugs and therapeutic agents for the treatment of diseases have been developed, but in terms of delivering drugs into the body, the problems of passing through biological barriers (e.g., skin, oral mucosa, blood-brain barrier, etc.) and the efficiency of drug delivery still remain to be improved.

Drugs are generally administered orally in the form of tablets or capsules, but many drugs cannot be effectively delivered only by the above administration method for reasons such as digestion or absorption in the gastrointestinal tract or disappearance by liver mechanisms. Additionally, some drugs cannot effectively diffuse through the intestinal mucosa. In addition, patient compliance is also problematic, such as in the case of critically ill patients who need to take medications at specific intervals or cannot take medications.

Another common technique for drug delivery is the use of conventional needles. While this method is more effective than oral administration, it has problems such as pain at the injection site, local skin damage, bleeding and disease infection at the injection site.

Influenza vaccines are also in need of a method for stably maintaining the activity of an antigen and saving the dosage. In order to solve the above problems, the inventors of the present invention developed the present invention by loading an influenza vaccine into a microneedle structure.

DISCLOSURE

Technical Problem

As such, the inventors of the present invention completed the present invention as a result of diligent efforts to melt the tip of a needle while penetrating the skin after the microneedle structure is attached to the human skin or pressure is applied while in contact, so as to deliver drug ingredients included in the needle to the human body.

Accordingly, an object of the present invention is to provide a composition including an influenza vaccine, a water-soluble polymer and an additive.

In addition, another object of the present invention is to provide an influenza vaccine soluble microneedle manufactured by the above composition, wherein the influenza vaccine soluble microneedle includes a support part, a middle part and a tip part.

Still another object of the present invention is to provide an influenza vaccine soluble microneedle array, including the influenza vaccine soluble microneedle; and a substrate layer for supporting the microneedle.

Technical Solution

The terms used in the present specification are used for descriptive purposes only and should not be construed as limiting. Singular expressions include plural expressions unless the context clearly dictates otherwise. In the present specification, it will be further understood that the terms "include" or "have" specify the presence of stated features, integers, steps, operations, elements, parts and/or combinations thereof, but do not preclude the presence or addition of one or more other features, integers, steps, operations, elements, parts and/or combinations thereof. Unless defined otherwise, all terms used herein, including technical or scientific terms, have the same meaning as commonly understood by a person of ordinary skill in the art to which the exemplary embodiments pertain. Terms such as those defined in commonly used dictionaries should be interpreted as having a meaning consistent with the meaning in the context of the related art, and unless explicitly defined in the present application, it should not be interpreted in an ideal or excessively formal meaning.

In order to achieve the above objects, the present invention provides an influenza vaccine composition, including an influenza vaccine, a water-soluble polymer and an additive.

In an exemplary embodiment, a solvent of the influenza vaccine included in the composition may be any one selected from the group consisting of phosphate buffer, acetate buffer, citrate buffer, glycine buffer, ammonium acetate buffer, succinate buffer, pyrophosphate buffer, Tris-acetate buffer, phosphate buffered saline and Tris-buffered saline.

In an exemplary embodiment, the water-soluble polymer included in the composition may be at least one selected from the group consisting of hydroxyethyl starch, hydroxypropylmethyl starch, gelatin, pullulan, dextran, sodium chondroitin sulfate, sodium hyaluronate, carboxymethylcellulose, polyvinylpyrrolidone, polyoxyethylene polyoxypropylene glycol, polyethylene glycol and polyvinyl alcohol, and wherein the water-soluble polymer is included at 1% or more and 50% or less in the total composition.

In an exemplary embodiment, the additive included in the composition may be at least one selected from the group consisting of trehalose, sucrose, calcium D-gluconate and arginine, and wherein the final concentration of the additive is 1% to 20% in the total composition.

In an exemplary embodiment, when the additive is included in two types, the two additives may be trehalose and sucrose, and the concentrations thereof may be 1% to 10%, respectively in the total composition.

In an exemplary embodiment, the influenza vaccine may be at least one selected from the group consisting of a live attenuated vaccine (LAV) or inactivated vaccine, a replicating viral vector (VVr), virus-like particles, a subunit vaccine, a non-self-replicating virus (viral vector, non-replicating), a synthetic vaccine or a genetically engineered vaccine.

In an exemplary embodiment, the influenza vaccine may be a polyvalent vaccine.

In addition, the present invention provides an influenza vaccine soluble microneedle manufactured by the composition, wherein the influenza vaccine soluble microneedle includes a support part, a middle part and a tip part.

In an exemplary embodiment, the composition may be positioned in the middle part, and the composition positioned in the middle part may be located in a core part or separated into layers.

In an exemplary embodiment, the middle part may be formed on the support part and include the composition, wherein when the middle part is made of a hydrophilic material, the height H2 of the middle part is inversely proportional to the thickness T of the tip part outside the middle part, and wherein when the middle part is made of a hydrophobic material, the height H2 of the middle part is constant regardless of the thickness T of the tip part outside the middle part.

In an exemplary embodiment, the thickness T of the tip part outside the middle part may be inversely proportional to the fluidization process time for forming the middle part and the tip part, is the smallest at a joint surface of the middle part and the support part or is uniform throughout the middle part, and wherein when the total height H of the support part, the middle part and the tip part and the height H1 of the support part are constant, the height H2 of the middle part and the height H3 from a tip of the middle part to a tip of the tip part are inversely proportional.

In addition, the present invention provides an influenza vaccine soluble microneedle array, including the influenza vaccine soluble microneedle; and a substrate layer for supporting the microneedle.

In an exemplary embodiment, the microneedle array may further include a microneedle including an immune enhancer.

In an exemplary embodiment, the microneedles may be regularly arranged at regular intervals.

In an exemplary embodiment, the height of the microneedle may be 500 to 1,000 μm.

In an exemplary embodiment, the microneedle may be in the form of an influenza vaccine patch including a support on the back of the microneedle array.

In an exemplary embodiment, the vaccine patch may include a marker formed on one side or the other side of the support to display predetermined information, and wherein the marker is formed to change color as at least one external stimulus of heat, light, moisture and pressure is applied after the microneedle is inserted into the skin.

In an exemplary embodiment, the marker may be formed such that the color changes over time after the microneedle is inserted into the skin.

In an exemplary embodiment, the marker may include a reactive material capable of undergoing an oxidation reaction, wherein the color change is made by an oxidation reaction of the reactant, and wherein the time required for the color change to be completed is formed to take 10 minutes or more.

In an exemplary embodiment, the marker may include a QR code (Quick Response code) or text.

In addition, the present invention provides a method for manufacturing a microneedle, including the steps of forming the influenza vaccine composition; forming a microneedle shape; and solidifying a viscous solution into the microneedle shape.

In an exemplary embodiment of the present invention, the step of forming may be at least one selected from the group consisting of fluidization, molding, centrifugal lithography and droplet-born air blowing.

Advantageous Effects

According to the influenza vaccine soluble microneedle and the influenza vaccine patch including the same according to the present invention, the convenience of inoculation can be improved compared to the conventional intramuscular injection vaccine, and since more immune cells are distributed in the dermal layer of the skin than in the muscle, it has a more excellent immune effect. In addition, since the needle itself is decomposed, there is no medical waste, and since it does not require refrigeration distribution as a solid form, it can be expected to increase storage stability.

DESCRIPTION OF DRAWINGS

FIG. 9 shows the results of quantitative analysis of the influenza vaccine loaded on the microneedle.

FIG. 10 shows experimental groups and experimental procedures for mouse inoculation experiments.

FIG. 11 shows the antibody titer measurement results after inoculation with Flu-DMN.

FIG. 12 shows the results of measuring neutralizing antibody titers after Flu-DMN inoculation.

MODES OF THE INVENTION

Figure 1:
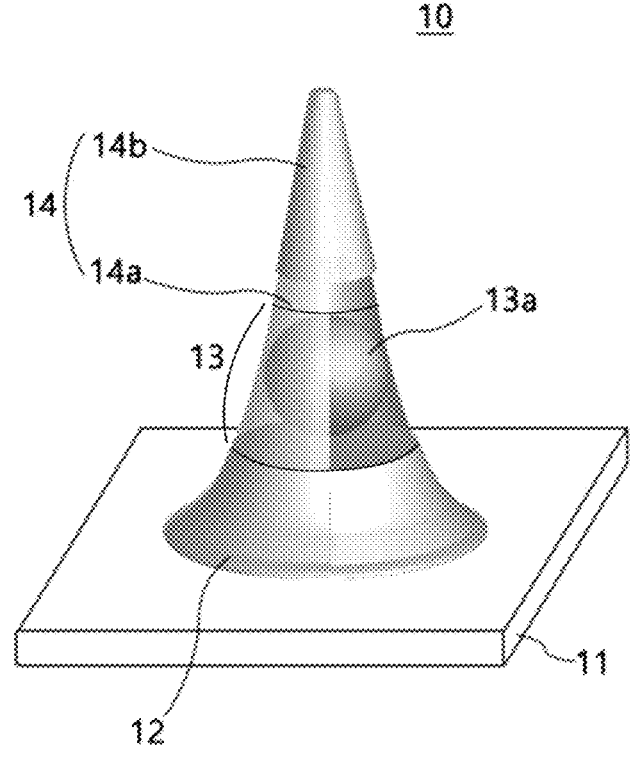
FIG. 1 is a perspective diagram showing the microneedle structure according to an exemplary embodiment of the present invention.
Figure 2:
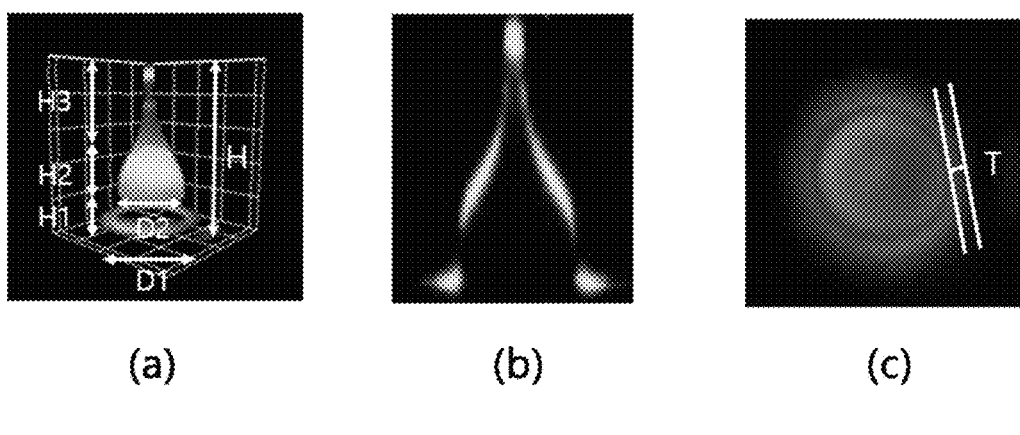
FIG. 2(a)-2(c) is a diagram showing each factor and shell structure of the microneedle structure of the present invention.

Hereinafter, the present invention will be described in more detail.

As described above, the present invention relates to a soluble microneedle containing an influenza vaccine, and when the microneedle structure is attached to the human skin or pressure is applied while in contact, it melts while the tip of the needle penetrates the skin, and the drug component contained in the needle may be delivered to the human body. In the case of delivering an influenza vaccine using a microneedle, it is important to stably maintain the activity of an antigen, and thus, the inventors of the present invention maximized the stability of a drug by adding specific additives at a specific composition ratio, and confirmed that by limiting the position of the drug to the central portion of the microneedle, not only the stability of the drug increased, but also the skin penetration and drug delivery effect became remarkable.

Accordingly, in one aspect, the present invention provides an influenza vaccine composition including an influenza vaccine, a water-soluble polymer and an additive.

As used herein, the term "vaccine" is used in the broadest sense to mean a composition that positively affects the immune response of a subject. The vaccine composition provides a humoral immune response, for example, an enhanced systemic/local immune response induced by the antibody, as well as a cell-mediated immune response, for example, a cytotoxic T-lymphocyte response (CTL) and the like to the inoculated subject.

According to a preferred embodiment of the present invention, the viral antigen included in the influenza vaccine soluble microneedle of the present invention includes an influenza virus-derived antigen. The antigen refers to an antigen capable of inducing an immune response among viral components, and preferably, it may be the hemagglutinin globular domain (HAgd) of influenza virus and the antigen or a fragment thereof of influenza type A (H1N1) strain, influenza type A (H3N2) strain and B strain.

According to a preferred embodiment of the present invention, the vaccine of the present invention is a live-attenuated vaccine (LAV) or inactivated vaccine, a self-replicating viral vector (VVr, replicating), virus-like particles, a subunit vaccine, a non-self-replicating virus vector (VVnr, Viral vectors, non-replicating), a synthetic vaccine or a genetically engineered vaccine, and preferably, an inactivated vaccine. The influenza vaccine composition of the present invention may induce an excellent immune response even with a low dose of antigen.

According to a preferred embodiment of the present invention, the vaccine may be a polyvalent vaccine. A polyvalent vaccine is a vaccine with multiple antigens, and refers to an aspect that aims to form acquired immunity against a single vaccine strain against multiple pathogens. It is made by mixing many types of the same species, such as human influenza vaccine or polio vaccine, that is, A1, A2 and B types for influenza, and types II, I and III for polio. These pathogens are divided into several serotypes, and when a patient is vaccinated with a separately included vaccine (monovalent vaccine), it is not helpful if the disease type occurs in a completely different type from the vaccine, and thus, polyvalent vaccines are used.

In this case, the pathogens targeted by the polyvalent vaccine may be pathogens that cause complex diseases in vivo, and in this case, the polyvalent vaccine has the advantage of preventing complex diseases. In addition, pathogens that are targets of polyvalent vaccines may cause major diseases that cause the most major damage to living organisms, and in this case, polyvalent vaccines have the advantage of forming immunity against diseases with the highest risk.

Pharmaceutically acceptable carriers included in the influenza vaccine composition of the present invention are commonly used in formulation, and include lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil and the like, but the present invention is not limited thereto. The vaccine composition of the present invention may further include lubricants, wetting agents, sweeteners, flavoring agents, emulsifiers, suspending agents and preservatives in addition to the above components.

The influenza vaccine composition of the present invention may include a vaccine adjuvant as an additive, and the adjuvant is a pharmacological or immunological substance added to change the effect of other substances. It may be added to a vaccine to increase the immune response to produce more antibodies for longer immunity, thereby minimizing the amount of antigen inoculated. Adjuvants may also increase the effectiveness of vaccines by modulating certain immune system cells to immunize.

Adjuvants include, for example, chemokines (e.g., defensins, HCC-1), HCC-4, MCP-1, MCP-3, MCP-4, MIP-1$\alpha$, MIP-1$\beta$, MIP-15, MIP-3a, MIP-2, RANTES, other ligand cytokines (e.g., IL-1 $\beta$, IL-2, IL-6, IL-8, IL-10, IL-12, IFN-$\gamma$, TNF-$\alpha$, GM-CSF) of chemokine receptors (e.g., CCR1, CCR-2, CCR-5, CCR-6, CXCR-1) cytokines, other protein ligands of receptors for the corresponding cytokines, heat shock proteins and derivatives thereof, *Leishmania* homologs of E1F4a and derivative bacteria thereof, ADP-ribosylated exotoxins and derivatives thereof (e.g., genetic mutants, A and/or B subunit-containing fragments, chemically toxined versions), bacterial ADP-ribosylated exotoxins or chemical conjugates or genetic recombinants including derivatives thereof, C3D tandem arrays and superantigens, but the present invention is not limited thereto (Nohria, et al. (Biotherapy, 7:261-269, 1994 for other useful adjuvants) and Richards, et al. (in Vaccine Design, Eds. Powell, et al., Plenum Press, 1995)).

The appropriate dosage of the influenza vaccine composition of the present invention may be prescribed in various ways depending on factors such as formulation method, administration method, patient's age, weight, gender, morbid condition, food, administration time, administration route, excretion rate and response sensitivity.

In the present invention, when the optimal combination and ratio of polymers and additives additionally included in addition to the influenza vaccine are specified, the stability of the influenza vaccine may increase and the solid form may be maintained, thereby stably maintaining the activity of the antigen.

In a specific embodiment of the present invention, the influenza vaccine composition may preferably refer to a viscous solution. In this case, additives for maintaining the stability of the vaccine and polymers for maintaining the shape of the solid phase may be included as additional excipients.

Exemplary excipients may include, for example, buffers, carbohydrates, polymers, amino acids, peptides, surfactants, proteins, non-volatile non-aqueous solvents, acids, bases, antioxidants and saccharin.

At least one buffering agent may be used as part of the at least one excipient. A buffer may generally function to stabilize pH in the step of preparing a soluble microneedle. The specific buffer used may be appropriately selected by a person skilled in the art according to the content of the influenza vaccine of the present invention.

The influenza vaccine composition of the present invention may also include a vaccine stabilizer, and any material for stabilizing the vaccine composition may be used without limitation, and may include sulfobutyl ether beta cyclodextrin (SBECD), meglumine or a salt thereof.

In an exemplary embodiment, the solvent of the influenza vaccine included in the composition may be any one selected from the group consisting of phosphate buffer, acetate buffer, citrate buffer, glycine buffer, ammonium acetate buffer, succinate buffer, pyrophosphate buffer, Tris-acetate buffer, phosphate buffered saline and Tris-buffered saline.

In a specific exemplary embodiment of the present invention, phosphate buffered saline (hereinafter, referred to as 'PBS'), ammonium acetate buffer and potassium phosphate buffer were used to change the solvent of the vaccine, but the present invention is not limited thereto.

In an exemplary embodiment, the water-soluble polymer included in the composition may be at least one selected from the group consisting of hydroxyethyl starch, hydroxy-propylmethyl starch, gelatin, pullulan, dextran, sodium chondroitin sulfate, sodium hyaluronate, carboxymethylcel-lulose (CMC), polyvinylpyrrolidone (PVP), polyoxyethyl-ene polyoxypropylene glycol, polyethylene glycol and poly-vinyl alcohol (PVA), but it may be used without limitation as long as it is a biocompatible water-soluble polymer. The water-soluble polymer may be characterized in that it is included at 1% or more and 50% or less in the total viscous solution composition. When the water-soluble polymer is included in an amount of 1% or less of the total viscous solution composition, it may be difficult to form the com-position into solid microneedles, and the physical strength of the microneedles may be insufficient to penetrate the skin. When the water-soluble polymer is included in an amount of 50% or more of the total viscous solution composition, it may be difficult to homogenize the polymer and the vaccine, and the release rate of the vaccine loaded on the microneedle may be significantly reduced.

In the present invention, silk fibroin may be additionally included in the water-soluble polymer to exhibit sustained release of the microneedle. As used herein, the term "fibroin" refers to an insoluble protein included in silk produced by other genera of moths, such as house silkworm larvae and the like. As used herein, the term "silk" may refer to *Bombyx mori* silkworm (home silkworm) or Tussah (giant silkworm, wild silkworm) and may refer to fibroin and silk itself extracted from silkworms, but is not limited thereto.

The silk fibroin may include, for example, regenerated silk fibroin and/or recombinant silk fibroin, and may be included in a form applied to a soluble base of the influenza vaccine composition of the present invention.

At least one carbohydrate, including mixtures of carbo-hydrates, may be used for at least a portion of the at least one excipient. The carbohydrate may be a saccharide, including mono-, di- and polysaccharides, and may include, for example, non-reducing sugars such as raffinose, stachyose, sucrose and trehalose; and reducing sugars such as mono-saccharides and disaccharides. Exemplary monosacharides may include apiose, arabinose, digitoxose, fucose, fructose, galactose, glucose, gulose, hamamelose, idose, lyxose, man-nose, ribose, tagatose, sorbitol, xylitol and xylose. Exem-plary disaccharides may include, for example, sucrose, trehalose, cellobiose, gentiobiose, lactose, lactulose, malt-ose, melibiose, primeverose, rutinose, scillabiose, sophorose, turanose and vicianose. In other aspects, sucrose, trehalose, fructose, maltose or combinations thereof may be utilized. All optical isomers of exemplified sugars (D, L and racemic mixtures) are also included herein.

Polysaccharides may include, for example, starches such as hydroxyethyl starch, pregelatinized corn starch, pen-tastarch, dextrin, dextran or dextran sulfate, gamma-cyclo-dextrin, alpha-cyclodextrin, beta-cyclodextrin, glucosyl-al-pha-cyclodextrin, maltosyl-alpha-cyclodextrin, glucosyl-beta-cyclodextrin, maltosyl-beta-cyclodextrin, 2-hydroxy-beta-cyclodextrin, 2-hydroxypropyl-beta-cyclodextrin, 2-hydroxypropyl-gamma-cyclodextrin, hydroxyethyl-beta-cyclodextrin, methyl-beta-cyclodextrin, sulfobutylether-al-pha-cyclodextrin, sulfobutylether-beta-cyclodextrin, and sulfobutylether-gamma-cyclodextrin. In exemplary embodi-ments, hydroxyethyl starch, dextrin, dextran, gamma-cyclo-dextrin, beta-cyclodextrin or combinations thereof may be used. In exemplary embodiments, dextrans having an aver-age molecular mass of 35,000 to 76,000 may be used.

The at least one carbohydrate may be a cellulose. Suitable celluloses may include, for example, hydroxyethyl cellulose (HEC), methyl cellulose (MC), microcrystalline cellulose, hydroxypropyl methyl cellulose (HPMC), hydroxyethylm-ethyl cellulose (HEMC), hydroxypropyl cellulose (HPC) and mixtures thereof.

At least one amino acid may be used for at least a portion of the at least one excipient. Suitable amino acids may include, for example, lysine, histidine, cysteine, glutamate, lysine acetate, sarcosine, proline, threonine, asparagine, aspartic acid, glutamic acid, glutamine, isoleucine, leucine, methionine, phenylalanine, serum tryptophan, tyrosine, valine, alanine, arginine and glycine. In many cases, the salt form of the amino acids may be used to increase the aqueous solubility of the amino acid in an aqueous media or formu-lation.

At least one peptide may be used for at least a portion of the at least one excipient. The amino acids making up the peptide may be the same or at least some may be different from each other. Suitable polyamino acids (the same amino acids) may include, for example, polyhistidine, polyaspartic acid and polylysine.

At least one protein may be used for at least a portion of the at least one excipient. Suitable proteins may include, for example, human serum albumin and bioengineered human albumin.

At least one saccharin may be used for at least a portion of the at least one excipient. In one example, the saccharin is saccharin sodium dihydrate.

At least one lipid may be used for at least a portion of the at least one excipient. In one example, the lipid may be dipalmitoylphosphatidylcholine (DPPC).

At least one acid and/or base may be used for at least a portion of the at least one excipient. For example, at least one weak acid, weak base, strong acid, strong base, or some combination thereof may be used. Acids and bases can serve the purpose of solubilizing or stabilizing the local anesthetic and/or the dose-extending component. These acids and bases can be referred to as counterions. These acids and bases may be organic or inorganic. Exemplary weak acids include, for example, acetic acid, propionic acid, pentanoic acid, citric acid, succinic acid, glycolic acid, gluconic acid, glucuronic acid, lactic acid, malic acid, pyruvic acid, tartaric acid, tartronic acid, fumaric acid, glutamic acid, aspartic acid, malonic acid, butyric acid, crotonic acid, digylcolic acid and glutaric acid. Exemplary strong acids include, for example, hydrochloric acid, hydrobromic acid, nitric acid, sulfonic acid, sulfuric acid, maleic acid, phosphoric acid, benzene sulfonic acid and methane sulfonic acid. Exemplary weak bases include, for example, ammonia, morpholine, histidine, lysine, arginine, monocthanolamine, dietha-nolamine, triethanolamine, tromethamine, methylglucamine and glucosamine. Exemplary strong bases include, for example, sodium hydroxide, potassium hydroxide, calcium hydroxide, and magnesium hydroxide.

At least one surfactant may be used for at least a portion of the at least one excipient. The at least one surfactant may be amphoteric, cationic, anionic or nonionic. Suitable sur-factants may include, for example, lecithin, polysorbates (e.g., polysorbate 20, polysorbate 40, and polysorbate 80), glycerol, sodium lauroamphoacetate, sodium dodecyl sul-fate, cetylpyridinium chloride (CPC), dodecyltrimethyl ammonium chloride (DoTAC), sodium desoxycholate, ben-zalkonium chloride, sorbitan laurate and alkoxylated alco-hols (such as laureth-4).

At least one inorganic salt may be used for at least a portion of the at least one excipient. Suitable inorganic salts may include, for example, sodium chloride and potassium chloride.

A non-volatile, non-aqueous solvent may also be used for at least a portion of the at least one excipient. Examples may include propylene glycol, dimethylsulfoxide, glycerin, 1-methyl-2-pyrrolidinone, N,N-dimethylformamide and the like.

At least one antioxidant may be used for at least a portion of the at least one excipient. Suitable antioxidants may include, for example, sodium citrate, citric acid, ascorbic acid, methionine, sodium ascorbate and combinations thereof.

In an exemplary embodiment, the additive included in the composition may be at least one selected from the group consisting of trehalose, sucrose, calcium D-gluconate and arginine, and the total concentration of the additive may be 1% to 20% in the total composition.

In an exemplary embodiment, when the additive is included in two types, preferably, the additives are trehalose and sucrose, and the concentrations are 1% to 10%, respectively in the total composition.

In an exemplary embodiment, when the influenza vaccine composition is composed of hyaluronic acid, trehalose, sucrose and influenza vaccine, the hyaluronic acid may be included at 10 to 30 wt. %, the trehalose may be included at 1 to 5 wt. %, the sucrose may be included at 1 to 5 wt. %, and the influenza vaccine may be included at 0.1 to 1 wt. % based on the viscous composition, and preferably, the hyaluronic acid may be included at 15 to 25 wt. %, the trehalose may be included at 2 to 4 wt. %, the sucrose may be included at 2 to 4 wt. %, and the influenza vaccine may be included at 0.3 to 0.8 wt. %, but the present invention is not limited thereto. Wt. % is based on the total content of the viscous composition.

In an exemplary embodiment of the present invention, if the combination and ratio of the additives are not as described above, the solid activity may not be sufficiently exhibited, or the stability of the influenza vaccine may not be significantly displayed.

In addition, the present invention provides an influenza vaccine soluble microneedle manufactured by the composition, wherein the influenza vaccine soluble microneedle is composed of a support part 12, a middle part 13 and a tip part 14.

According to an aspect of the present invention, the microneedle includes a middle part 13 in which the influenza vaccine is loaded in the form of a core or a layer, and the upper and lower ends except for the middle part 13 may be configured with a microneedle including a tip part 14 and a support part 12 on which the influenza vaccine is not loaded, respectively.

The middle part 13 may be composed of an influenza vaccine, an additive for maintaining the activity of the vaccine, an immune enhancer for improving immune efficacy and a polymer for maintaining a solid form.

The tip part 14 may be composed of a polymer having sufficient strength to physically penetrate the skin layer and an additive for rapid dissolution in the skin.

The support part 12 may be composed of a polymer for the microneedle to penetrate the skin and have sufficient strength to deliver all the vaccine contained therein, an additive for rapid dissolution in the skin and an additive for recovering microscopic wounds caused by skin penetration.

As used herein, the term "immune enhancer" generally refers to any substance that increases a humoral or cell-mediated immune response to an antigen.

According to a preferred embodiment of the present invention, the influenza vaccine soluble microneedle of the present invention may include a pharmaceutically acceptable carrier, and the description thereof is described below.

Based on the microneedle solid content, the hyaluronic acid may be included at 70 to 75 wt. %, the trehalose may be included at 10 to 15%, the sucrose may be included at 10 to 15%, and the influenza vaccine may be included at 1 to 3 wt. %, and preferably, the hyaluronic acid may be included at 72 to 74 wt. %, the trehalose may be included at 11 to 13%, the sucrose may be included at 11 to 13%, and the influenza vaccine may be included at 1 to 2 wt. %, but the present invention is not limited thereto. Wt. % is based on the total microneedle content.

As shown in a specific exemplary embodiment of the present invention, by concentrating the influenza vaccine in the central portion at a specific composition ratio, the skin penetration is high and the drug delivery effect is excellent.

Therefore, according to an aspect of the present invention, the location of the composition is positioned in the middle part 13, and the composition located in the middle part 13 may be positioned in the core part 13a or separated into layers.

In this case, it may be surrounded by a biocompatible water-soluble polymer constituting the tip part 14 and the support part 12 for physically penetrating the skin layer and rapidly dissolving in the skin, and may be mounted on the microneedle structure without exposure. Alternatively, some side surfaces may be exposed.

The support part 12 is formed on the support body 11 at a constant height. The support part 12 is to assist in the quantitative delivery of the drug, and may be formed at a constant height such that the middle part 13 containing the drug can be sufficiently inserted into the skin. Thus, the support part 12 does not include a drug.

Through this, since the influenza vaccine soluble microneedle according to an exemplary embodiment of the present invention may sufficiently insert the middle part 13 containing the drug into the skin, it is possible to ensure the reliable quantitative delivery of the drug.

The middle part 13 is a portion for loading an effective drug and is formed on the support part 12. Herein, the middle part 13 may be made of a hydrophilic material or a hydrophobic material. As an example, the middle part 13 may include hyaluronic acid (HA) or polycaprolactone (PCL), but is not limited thereto. Moreover, the middle part 13 may be made of powder or liquid.

In this case, the middle part 13 may have various shapes depending on the material to be manufactured. For example, when the middle part 13 is made of a hydrophilic material, it may have a shape similar to that of the tip part 14. That is, the middle part 13 may be formed similar to the shape of the tip 14b of the tip part 14 because it is affected by the fluidization process.

Alternatively, when the middle part 13 is made of a hydrophobic material, it may be provided in a circular shape within the tip part 14. Herein, the shape of the middle part 13 is not particularly limited. However, the middle part 13 has a shape independent of the shape of the tip part 14. That is, unlike the case of the hydrophilic material, the middle part 13 may not be formed similarly to the shape of the tip 14b of the tip part 14 because it is hardly affected by the fluidization process.

The tip part 14 is for forming the overall shape of the vaccine soluble microneedle and is formed to cover the middle part 13 on the support part 12. Herein, the tip part 14 may be made of a polymer that is not loaded with a drug. The tip part 14 may include a cover layer 14a and a tip 14b.

The cover layer 14*a* is for protecting the drug of the middle part 13 and may completely cover the middle part 13 such that it is not exposed to the outside.

The tip 14*b* may have a sharp tip formed so as to be easily inserted into the skin. In this case, the tip part 14 may be made of a material having physically high strength or may be manufactured by a manufacturing process for this purpose.

Herein, the tip part 14 may be formed by centrifugal lithography using a fluidization process. Therefore, the shape of the tip part 14 may be changed according to the fluidization process time.

In this case, the relationship between the thickness T of the tip part 14 outside the middle part 13 and the height H2 of the middle part 13 may be determined according to the material forming the middle part 13. Herein, the thickness T of the tip part 14 outside the middle part 13 may be affected by the fluidization process time. That is, the thickness T of the tip part 14 outside the middle part 13 may be inversely proportional to the fluidization process time.

For example, when the middle part 13 is made of a hydrophilic material, the height H2 of the middle part 13 may be affected by the fluidization process time. More specifically, the height H2 of the middle part 13 may be inversely proportional to the thickness T of the tip part 14 outside the middle part 13. That is, the height H2 of the middle part 13 may increase as the thickness T of the tip part 14 outside the middle part 13 decreases.

In this case, the height H3 from the tip of the middle part 13 to the tip of the tip part 14 may decrease as the thickness T of the tip part 14 outside the middle part 13 decreases. Therefore, the height H3 from the tip of the middle part 13 to the tip of the tip part 14 may be proportional to the thickness T of the tip part 14 outside the middle part 13.

Herein, when the overall height H of the support part 12, the middle part 13 and the tip part 14 and the height H1 of the support part 12 are constant, the height H2 of the middle part 13 and the height H3 from the tip of the middle part 13 to the tip of the tip part 14 may be affected by the fluidization process time. In this case, since the height H2 of the middle part 13 increases in proportion to the fluidization process time, the height H2 of the middle part 13 and the height H3 from the tip of the middle part 13 to the tip of the tip part 14 may be in inverse proportion to each other.

As another example, when the middle part 13 is made of a hydrophobic material, the height H2 of the middle part 13 is not affected by the fluidization process time. That is, the height H2 of the middle part 13 may be constant regardless of the thickness T of the tip part 14 outside the middle part 13.

In this case, the thickness T of the tip part 14 outside the middle part 13 may be 1 to 50 μm. Herein, when the thickness T of the tip part 14 outside the middle part 13 is less than 1 μm, the tip part 14 does not provide sufficient strength and is therefore exposed to the outside of the middle part 13 or may leak from a cover layer 14*a*. Therefore, the vaccine soluble microneedle may not guarantee the safe protection of the drug.

On the other hand, when the thickness T of the tip part 14 outside the middle part 13 is more than 50 μm, the tip part 14 is formed more than necessary, and the material may be wasted without improving the effect of the tip part 14.

In addition, the thickness T of the tip part 14 outside the middle part 13 may be different for each position depending on the physical properties or shape of the middle part 13. For example, the thickness T of the tip part 14 outside the middle part 13 may be the smallest at the joint surface between the middle part 13 and the support part 12. Accordingly, the vaccine soluble microneedle may be easily manufactured without optimizing fluidization process conditions.

As another example, the thickness T of the tip part 14 outside the middle part 13 may be uniform throughout the middle part 13. As a result, the tip part 14 may more safely ensure the protection of the drug contained in the middle part 13.

In addition, the present invention provides an influenza vaccine soluble microneedle array, including the influenza vaccine soluble microneedle; and a substrate layer for supporting the microneedle.

When the microneedle array according to the present invention is applied to the mucous membrane or skin, the soluble microneedle may reach the mucous membrane or the skin, and the microneedle part is dissolved such that the influenza vaccine acts. The substrate of the microneedle array adheres to the curves of the mucous membrane or skin in a high-humidity environment, and the influenza vaccine contained in the substrate also induces a high antibody production effect.

When the microneedle array is applied to the skin, it is difficult to bend with appropriate hardness, and also, in order to make the influenza vaccine easy to penetrate, a microneedle array may be formed from a mixture of a high molecular weight polymer material having a weight average molecular weight of 100,000 or more and a low molecular weight polymer material having a weight average molecular weight of 50,000 or less. The weight average molecular weight of the high molecular weight polymer material is preferably 50,000 or more and 2,000,000 or less. In addition, the weight average molecular weight of the low molecular weight polymer material is preferably 1,000 or more and 50,000 or less. In an exemplary embodiment, the weight average molecular weight may be measured by gel permeation chromatography (GPC).

In an exemplary embodiment, the microneedle array may further include microneedles including an immune enhancer.

In an exemplary embodiment of the present invention, the microneedles may be regularly arranged at regular intervals.

In an exemplary embodiment, the height of the microneedle may be characterized to be 500 to 1,000 μm. Preferably it may be 600 to 950 μm, and more preferably, it may be 700 to 900 μm.

The support part 12 is formed at a constant height on the substrate layer. The support part 12 is to assist in the quantitative delivery of the drug, and it may be formed at a constant height such that the middle part 13 including the drug can be sufficiently inserted into the skin. Thus, the support part 12 does not include a drug.

Through this, since the microneedle according to an exemplary embodiment of the present invention may sufficiently insert the middle part 13 including the influenza vaccine into the skin, it is possible to ensure the reliable quantitative delivery of the drug.

As one aspect of the present invention, the microneedle array may be in the form of an influenza vaccine patch including a support on the back of the microneedle array.

The support may be manufactured in a size and shape that is easy to handle depending on the application site, and is preferably about 3 to 20 mm larger than the outer edge of the microneedle array. The thickness of the support may be the same as, thinner or thicker than the thickness of the microneedle array substrate, and it may be manufactured to be flexible and thin to support the microneedle array and to be easily handled during use.

The support preferably has adhesiveness to the mucous membrane or skin in order to reinforce the adhesion of the microneedle array to the mucous membrane or skin.

As one form for the adhesiveness of the support, a support in which an adhesive material is coated on the support, that is, a support coated with an adhesive may be used.

As the adhesive material, adhesives commonly used in patch formulations may be used, and for example, grades with adhesion to the wet surface of acrylic, silicone and rubber-based adhesives are preferred.

As another form of the adhesion of the support, the support may be water soluble. By using a low molecular weight water-soluble film such as polyvinylpyrrolidone (PVP), carboxymethylcellulose (CMC) or polyvinyl alcohol (PVA), adhesion may be exhibited by the moisture of the mucous membrane or skin. In this case, it is preferable to further laminate a water-insoluble polymer film on the opposite side of the water-soluble support so as not to adhere to the opposite side of the mucous membrane or skin to be applied.

The support includes a polymer having sufficient strength to allow the microneedle to permeate the skin and deliver all of the vaccine contained therein, and an additive for rapid dissolution in the skin. In addition, it may additionally include additives for recovering microscopic wounds caused by skin penetration, and any additives within the range selectable by a person skilled in the art may be used without limitation.

In the microneedle array and microneedle patch of the present invention, the amount of influenza vaccine included in the microneedle array per unit area and the size of the microneedle array may be appropriately set, such as for mucosa or skin.

In a specific exemplary embodiment, 61 microneedles having a length of 850±50 μm were arranged in each patch in the microneedle patch.

In an exemplary embodiment of the present invention, the vaccine patch includes a marker formed on one side or the other side of the support to display predetermined information, and the marker may be formed to change color as at least one external stimulus of heat, light, moisture and pressure is applied after the microneedle is inserted into the skin.

The information may include information about the microneedle and the microneedle patch. For example, it may include information about the type and dose of the administered substance that is administered into the body by the microneedle, product information and precautions therefor.

In the present exemplary embodiment, the user can immediately check the product name and product number by checking the character display. In addition, by scanning a QR code using a user terminal such as a smartphone, the user can easily and conveniently obtain a lot of information such as the type, dosage, product information, administration time and precautions of the drug administered into the body.

Furthermore, the marker may deliver other information in addition to the above information to a third party other than the user. For example, a medical staff or quarantine manager may be included as a third party, and a patient under the care of a medical staff or a person who enters or exits a specific facility or crosses a border may be a user.

In an exemplary embodiment of the present invention, the marker may be formed to change color as time elapses after the plurality of microneedles are inserted into the skin.

In an exemplary embodiment of the present invention, the marker includes a reactive material capable of undergoing an oxidation reaction, the color change is achieved by an oxidation reaction of the reactive material, and the time required for the color change to be completed may be formed to take 10 minutes or more.

The time required may be set to the time required for a certain amount of the influenza vaccine included in the microneedle, for example, 80% or more, to be administered into the body. More specifically, the time required may be set to be 10 minutes or more after the microneedle is inserted. In this way, by adjusting the minimum time required for the target amount of influenza vaccine to be administered into the body and the time required for the color of the marker to change, it is possible to deliver information about the actual application time associated with the dosage to the user.

In this case, the time required for the color of the marker to change can be derived through repetitive experiments performed while changing the type, concentration and selection of reaction materials and the selection of other materials to be mixed.

In an exemplary embodiment of the present invention, the marker may include a QR code (Quick Response code) or text. In the present specification, the QR code refers to a two-dimensional (matrix) type code that contains various information in a rectangular grid pattern in the horizontal and vertical directions.

In addition, the present invention provides a method for treating influenza by administering the influenza vaccine composition by applying the microneedle array including the influenza vaccine composition according to the present invention. The microneedle array may be in the form of a vaccine patch, and the administration method may be performed without limitation as long as it is a known method.

In addition, the present invention provides a method for manufacturing an influenza vaccine soluble microneedle, including the steps of forming the influenza vaccine composition; forming a microneedle shape; and solidifying a viscous solution into the microneedle shape.

In an exemplary embodiment of the present invention, the step of forming may be at least one selected from the group consisting of fluidization, molding, centrifugal lithography and droplet-born air blowing.

In a specific exemplary embodiment of the present invention, the microneedle was manufactured by including a first dispensing step of dispensing a first composition on a support; a drying step of drying the first composition to form a support part; a second dispensing step of dispensing a second composition including a drug on the support part; a third dispensing step of dispensing a third composition to cover the second composition on the support part; and a forming step of forming a middle part by the second composition and a tip part 14 by the third composition by fluidization and centrifugal lithography. In the first composition, sodium hyaluronate 30 kDa 65% (w/v), which is a water-soluble polymer, was included in PBS as a solvent, and a solution (second composition) having a composition finally containing the influenza vaccine was applied on the support. The third composition was applied with sodium hyaluronate 30 kDa 65% (w/v) and PBS as a solvent to cover the second composition, and afterwards, through fluidization and centrifugal lithography steps, a middle part was formed by the second composition, and a tip part was formed by the third composition.

When a microneedle is used, the influenza vaccine of the present invention is one of the promising fields that can show many advantages such as solving the cold chain problem, saving the dose, self-administration and the like. In addition, since the microneedle is in a solid form, the activity of the loaded antigen may be stably maintained compared to the liquid injection. Moreover, since the microneedle directly delivers the antigen to the dermal layer rich in immune-related cells (antigen-presenting cells), it is possible to expect a high antibody production effect even with a small amount of antigen.

Hereinafter, the present invention will be described in more detail through examples. These examples are only for exemplifying the present invention, and it will be apparent to those skilled in the art that the scope of the present invention is not to be construed as being limited by these examples.

Example 1

Primary Screening

Screening was performed by changing to three solvents such that it is possible to change the solvent of the vaccine and apply on the microneedle, minimize the loss and increase the recovery rate. Screening was performed with PBS, 150 mM ammonium acetate (pH 7.4) and 100 mM potassium phosphate (pH 7.4) as candidates, and the results are as follows.

TABLE 1

| Buffer exchange & concentration | Original | PBS | 150 mM ammonium acetate (pH 7.4) | 100 mM potassium phosphate (pH 7.4) |
|---|---|---|---|---|
| Protein conc. (μg/mL) | 516 | 22,500 | 16,600 | 20,400 |

TABLE 1-continued

| Buffer exchange & concentration | Original | PBS | 150 mM ammonium acetate (pH 7.4) | 100 mM potassium phosphate (pH 7.4) |
|---|---|---|---|---|
| HA conc. (μg/mL) | — | 6,500 | 4.492 | 5.356 |
| Volume (μL) | — | 500 | 85 | 112 |
| Total protein (μg) | — | 11,250 | 1,411 | 2,284.8 |
| Loss (μg) | | 2,166 | 1,169 | 1,169 |
| Recovery rate (%) | | 83.9 | 54.7 | 88.6 |

As a result of the primary screening, PBS was the most excellent in protein concentration, HA concentration and recovery rate, followed by phosphate and acetate.

Example 2

Secondary Screening

Eight viscous solutions were prepared and the type (carboxymethyl cellulose 250, gelatin from cold water fish) and concentration (1%, 5%, 10%) of polymer and the combination of additives (trehalose, arginine and sucrose, calcium D-gluconate) according to the solvent were confirmed. The influenza vaccine used in this case and the concentration of hemagglutinin in the influenza vaccine were maintained at 6.5 mg/mL. The compositions of the eight viscous solutions are shown in [Table 2] 10 below.

TABLE 2

| Viscous solution No. | Buffer | Influenza vaccine | Influenza vaccine hemagglutinin Concentration (mg/mL) | Polymer | Polymer concentration (w/v) | Additive 1 | Concentration of Additive 1 (w/v) | Additive 2 | Concentration of Additive 2 (w/v) |
|---|---|---|---|---|---|---|---|---|---|
| 1 | 100 mM potassium phosphate (pH 7.4) | A/Michigan/45/2015 reassortant virus (H1N1) | 6.5 | carboxymethyl cellulose 250 | 1% | Trehalose | 5% | Sucrose | 5% |
| 2 | 100 mM potassium phosphate (pH 7.4) | A/Michigan/45/2015 reassortant virus (H1N1) | 6.5 | carboxymethyl cellulose 250 | 1% | Arginine | 5% | Calcium D-gluconate | 5% |
| 3 | 100 mM potassium phosphate (pH 7.4) | A/Michigan/45/2015 reassortant virus (H1N1) | 6.5 | carboxymethyl cellulose 250 | 5% | Trehalose | 5% | Sucrose | 5% |
| 4 | 100 mM potassium phosphate (pH 7.4) | A/Michigan/45/2015 reassortant virus (H1N1) | 6.5 | carboxymethyl cellulose 250 kDa | 5% | Arginine | 5% | Calcium D-gluconate | 5% |
| 5 | 100 mM potassium phosphate (pH 7.4) | A/Michigan/45/2015 reassortant virus (H1N1) | 6.5 | Gelatin from cold water fish | 10% | Trehalose | 5% | Sucrose | 5% |
| 6 | 100 mM potassium phosphate (pH 7.4) | A/Michigan/45/2015 reassortant virus (H1N1) | 6.5 | Gelatin from cold water fish | 10% | Arginine | 5% | Calcium D-gluconate | 5% |
| 7 | 150 mM ammonium acetate (pH 7.4) | A/Michigan/45/2015 reassortant virus (H1N1) | 6.5 | carboxymethyl cellulose 250 kDa | 5% | Trehalose | 5% | Sucrose | 5% |
| 8 | Phosphate-buffered saline (pH 7.4) | A/Michigan/45/2015 reassortant virus (H1N1) | 6.5 | carboxymethyl cellulose 250 kDa | 5% | Trehalose | 5% | Sucrose | 5% |

Two samples were used for each solution, and the specific sample information therefor is shown in [Table 3]. In addition, the HA ratio (w/w), discharge amount (mg), HA amount (mg) and HA amount (μg) were shown. These are the results calculated such that 15 μg can be loaded per microneedle patch.

TABLE 3

| Viscous solution | Sample # | Solvent | Polymer | Additive | HA ratio (W/W) | Discharge amount (mg) | HA amount (mg) | HA amount (ug) |
|---|---|---|---|---|---|---|---|---|
| 1 | 1-3 | Phosphate | CMC 1% | TRE 5%, SUC 5% | 0.004841 | 2.7 | 0.0131 | 13.1 |
| | 1-4 | Phosphate | CMC 1% | TRE 5%, SUC 5% | 0.004841 | 2.7 | 0.0131 | 13.1 |
| 2 | 2-2 | Phosphate | CMC 1% | ARG 5%. CHG 5% | 0.004841 | 2.9 | 0.0140 | 14.0 |
| | 2-3 | Phosphate | CMC 1% | ARG 5%, CHG 5% | 0.004841 | 2.9 | 0.0140 | 14.0 |
| 3 | 3-1 | Phosphate | CMC 5% | TRE 5%, SUC 5% | 0.004674 | 3.4 | 0.0159 | 15.9 |
| | 3-2 | Phosphate | CMC 5% | TRE 5%, SUC 5% | 0.004674 | 3.5 | 0.0164 | 16.4 |
| 4 | 4-1 | Phosphate | CMC 5% | ARG 5%, CHG 5% | 0.004674 | 2.8 | 0.0131 | 13.1 |
| | 4-3 | Phosphate | CMC 5% | ARG 5% CHG 5% | 0.004674 | 3.0 | 0.0140 | 14.0 |
| 5 | 5-2 | Phosphate | FG 10% | TRE 5%, SUC 5% | 0.004480 | 4.0 | 0.0179 | 17.9 |
| | 5-3 | Phosphate | FG 10% | TRE 5%, SUC 5% | 0.004480 | 4.0 | 0.0179 | 17.9 |
| 6 | 6-2 | Phosphate | FG 10% | ARG 5%, CHG 5% | 0.004480 | 3.1 | 0.0139 | 13.9 |
| | 6-3 | Phosphate | FG 10% | ARG 5%, CHG 5% | 0.004480 | 2.9 | 0.0130 | 13.0 |
| 7 | 7-1 | Acetate | CMC 5% | TRE 5%, SUC 5% | 0.004674 | 1.9 | 0.0089 | 8.9 |
| | 7-3 | Acetate | CMC 5% | TRE 5%, SUC 5% | 0.004674 | 1.8 | 0.0084 | 8.4 |
| 8 | 8-1 | PBS | CMC 5% | TRE 5%, SUC 5% | 0.004674 | 2.5 | 0.0117 | 11.7 |
| | 8-3 | PBS | CMC 5% | TRE 5%, SUC 5% | 0.004674 | 2.5 | 0.0117 | 11.7 |

Figure 3:
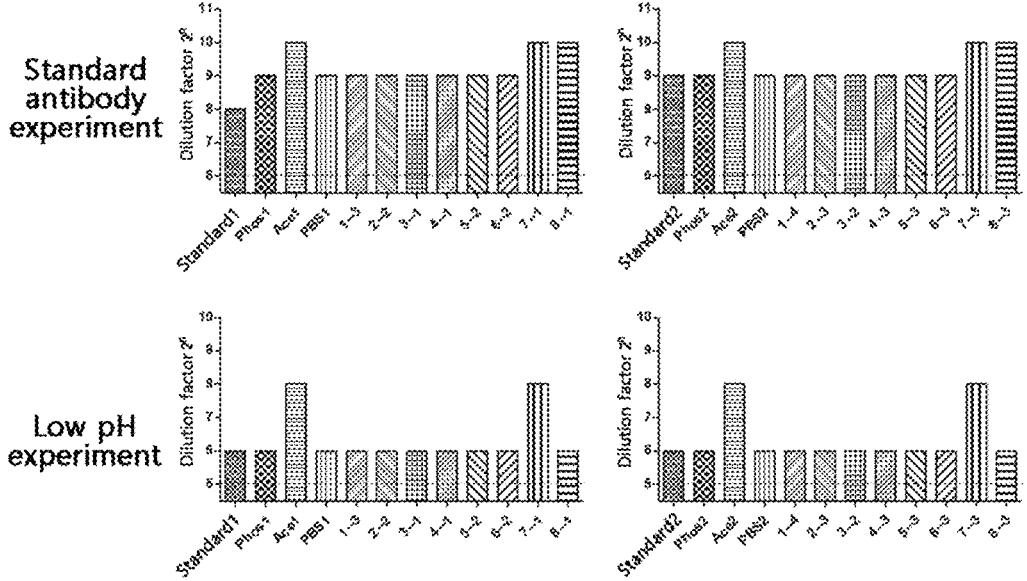
FIG. 3 shows the results of standard antibody experiments and low pH experiments according to the type and concentration of polymer and the combination of additive.
Figure 4:
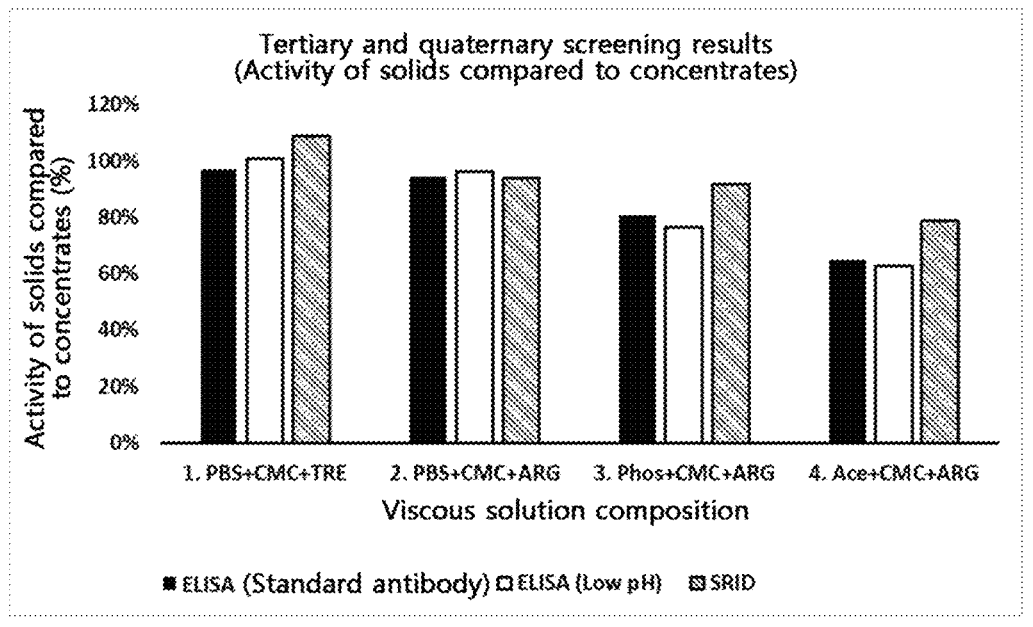
FIG. 4 shows the results of comparing the activity of solids against the concentrates for each composition of the viscous solution as a result of the tertiary and quaternary screening.

The results of the standard antibody experiments and the low pH experiments for the above samples are shown in FIG. 3.

Enzyme-Linked Immunosorbent Assay (ELISA)

The HA of influenza was quantitatively analyzed by using the antigen-antibody reaction. In the case of the standard antibody experimental method, the amount of HA bound to the antibody was quantified by coating a 96-well plate with the NIBSC standard antigen and processing a sample including influenza HA.

Low pH Experiments

In the case of the low pH experimental method, a 96-well plate was prepared similarly to the standard antibody experimental method, and samples including influenza HA were prepared under slightly acidic conditions similar to the Ph environment in the skin to quantify the amount of HA bound to the antibody.

As a result, the scores obtained by summarizing the ELISA results, the concentrate BSA assay and the SRID results from the eight samples are shown in [Table 4] below. As a result of scoring based on self-standards, PBS was ranked $1^{st}$, phosphate ranked $2^{nd}$ to $7^{th}$ and acetate ranked $8^{th}$.

TABLE 4

| | | Test group | | | | | | | | | | |
|---|---|---|---|---|---|---|---|---|---|---|---|---|
| | | | | | | | Solids | | | | | |
| | | Concentrates | | | | | | Phos | | | | Ace | PBS |
| | | Phos | Ace | PBS | 1 | 2 | 3 | 4 | 5 | 6 | 7 | 8 |
| Score | | 7.196 93 | 6.0376 78899 | 7.1456 89655 | 6.8043 48837 | 6.458 023 | 6.968 535 | 6.969 209 | 6.866 023 | 6.539 86 | 5.798 578 | 8.368 966 |
| Activity of solids compared to concentrates | | | | | 95% | 90% | 97% | 97% | 95% | 91% | 96% | 117% |
| Rank | | | | | 5 | 7 | 3 | 2 | 4 | 6 | 8 | 1 |

Based on these results, two types of PBS solids and one type of phosphate solids were selected. In addition, although the acetate solid activity was ranked $8^{th}$, one type was selected because of its good activity in the reference, and then, the tertiary screening was performed.

Example 3

Tertiary Screening, ELISA

The tertiary and quaternary screening samples are shown in [Table 5]. Two types of PBS solids and one type of phosphate solids, which showed excellent results in the secondary screening, were included, and acetate solids were included in the experimental group.

TABLE 5

| No. | Test group | Details | Remark |
|---|---|---|---|
| 1 | Solids | Phosphate buffer | |
| 2 | (experimental | Acetate buffer | |

TABLE 5-continued

| No. | Test group | Details | Remark |
|---|---|---|---|
| 3 | group) | PBS buffer | |
| 4 | | PBS buffer | |
| 5 | Concentrates | PBS buffer | Same concentrate |
| 6 | | Phosphate buffer | used to make |
| 7 | | Acetate buffer | solids |
| 8 | Standard antigen | NIBSC standard antigen | — |
| 9 | Solids (Blank) | Polymer1, Excipient1 | — |
| 10 | | Polymer1, Excipient2 | — |
| 11 | | Polymer2, Excipient1 | — |
| 12 | | Polymer2, Excipient2 | — |

The detailed composition information of the solid experimental group in the table above is shown in [Table 6].

TABLE 6

| No. | Buffer | Influenza vaccine | Influenza vaccine hemagglutinin Concentration (mg/ml) | Polymer | Polymer concentration (w/v) | Additive 1 | Concentration of Additive 1 (w/v) | Additive 2 | Concentration of Additive 2 (w/v) |
|---|---|---|---|---|---|---|---|---|---|
| 1 | 100 mM potassium phosphate (pH 7.4) | A/Michigan/45/2015 reassortant virus (H1N1) | 6.5 | carboxymethyl cellulose 250 kDa | 5% | Trehalose | 5% | Sucrose | 5% |
| 2 | 150 mM ammonium acetate (pH 7.4) | A/Michigan/45/2015 reassortant virus (H1N1) | 6.5 | carboxymethyl cellulose 250 kDa | 5% | Trehalose | 5% | Sucrose | 5% |
| 3 | Phosphate-buffered saline (pH 7.4) | A/Michigan/45/2015 reassortant virus (H1N1) | 6.5 | carboxymethyl cellulose 250 kDa | 5% | Trehalose | 5% | Sucrose | 5% |
| 4 | Phosphate-buffered saline (pH 7.4) | A/Michigan/45/2015 reassortant virus (H1N1) | 6.5 | carboxymethyl cellulose 250 kDa | 5% | Arginine | 5% | Calcium D-gluconate | 5% |

The results are shown in [Table 7], and the resulting values represent the scores obtained by summarizing the ELISA results, the concentrate BCA assay and the SRID results.

TABLE 7

| | Standard Antibody Experiment 1 | | | |
|---|---|---|---|---|
| | Phos | Ace | PBS | |
| Test group | 1--1 | 2--1 | 3--1 | 4--1 |
| Result values | 2.916594 | 2.233676 | 2.950281 | 2.844101 |
| Activity of solids compared to concentrates | 82% | 62% | 98% | 95% |

TABLE 7-continued

| | Standard Antibody Experiment 2 | | | |
| --- | --- | --- | --- | --- |
| | Phos | Ace | PBS | |
| Test group | 1--2 | 2--2 | 3--2 | 4--2 |
| Result values | 2.568178 | 2.173461 | 2.510393 | 2.464888 |
| Activity of solids compared to concentrates | 80% | 67% | 96% | 94% |

| | Low pH Experiment 1 | | | |
| --- | --- | --- | --- | --- |
| | Phos | Ace | PBS | |
| Test group | 1--1 | 2--1 | 3--1 | 4--1 |
| Result values | 3.226634 | 2.55998 | 3.488764 | 3.397753 |
| Activity of solids compared to concentrates | 83% | 64% | 106% | 104% |

TABLE 7-continued

| | Low pH Experiment 2 | | | |
| --- | --- | --- | --- | --- |
| | Phos | Ace | PBS | |
| Test group | 1--2 | 2--2 | 3--2 | 4--2 |
| Result values | 2.965069 | 2.475353 | 3.223315 | 3.005899 |
| Activity of solids compared to concentrates | 71% | 62% | 96% | 89% |

As a result of self-standard scoring, PBS solids activity was the highest. Blank solids had no ELISA binding.

Example 4

Quaternary Screening, SRID

The amount of bemagglutinin (HA) protein in the vaccine was measured by using single radial immune diffusion (SRID). The contents of the samples used for screening are shown in [Table 8] below.

TABLE 8

| No. | Name | Buffer | Influenza vaccine | Influenza vaccine hemagglutinin Concentration (mg/ml) | Polymer | Polymer concentration (w/v) | Additive 1 | Concentration of Additive 1 (w/v) | Additive 2 | Concentration of Additive 2 (w/v) |
| --- | --- | --- | --- | --- | --- | --- | --- | --- | --- | --- |
| 1 | Solid PBS1 | Phosphate-buffered saline (pH 7.4) | A/Michigan/45/2015 reassortant virus (H1N1) | 6.5 | carboxymethyl cellulose 250 kDa | 5% | Trehalose | 5% | Sucrose | 5% |
| 2 | Solid PBS2 | Phosphate-buffered saline (pH 7.4) | A/Michigan/45/2015 reassortant virus (H1N1) | 6.5 | carboxymethyl cellulose 250 kDa | 5% | Arginine | 5% | Calcium D-gluconate | 5% |
| 3 | Solid pho | 100 mM potassium phosphate (pH 7.4) | A/Michigan/45/2015 reassortant virus (H1N1) | 6.5 | carboxymethyl cellulose 250 kDa | 5% | Trehalose | 5% | Sucrose | 5% |
| 4 | Solid ace | 150 mM ammonium acetate (pH 7.4) | A/Michigan/45/2015 reassortant virus (H1N1) | 6.5 | carboxymethyl cellulose 250 kDa | 5% | Trehalose | 5% | Sucrose | 5% |

As a result, as shown in [Table 9] below, the activity was good in the order of PBS>Phosphate>Acetate as a result of the SRID experiment, and the blank solids did not have SRID binding.

TABLE 9

| | | | | Primary | | | Secondary | | |
| --- | --- | --- | --- | --- | --- | --- | --- | --- | --- |
| No. | Solvent | Polymer | Additive | Expected HA amount | HA amount as a result of SRID | Activity (%) | Expected HA amount | HA amount as a result of SRID | Activity (%) |
| 1 | PBS | CMC | TRE + SUC | 21.2 | 23.1 | 109.0% | 22.1 | 24.0 | 108.6% |
| 2 | PBS | CMC | ARG + CHG | 26.3 | 24.8 | 94.2% | 27.2 | 25.2 | 93.9% |
| 3 | Phos | CMC | ARG + CHG | 37.0 | 33.9 | 91.7% | 38.6 | 35.4 | 91.7% |
| 4 | Ace | CMC | ARG + CHG | 31.1 | 24.5 | 78.7% | 31.7 | 24.9 | 78.6% |

Figure 5:
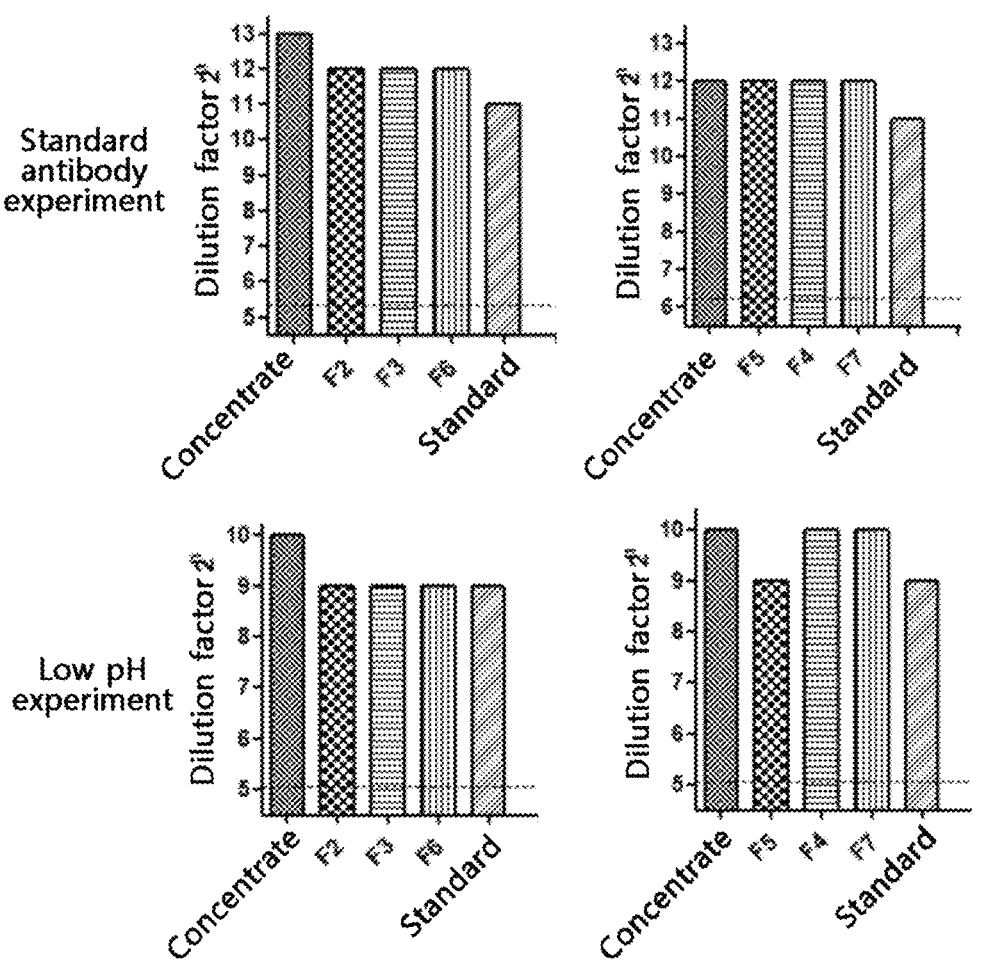
FIG. 5 is a result of analyzing the activity of each microneedle manufacturing process, and shows the results of standard antibody experiments and low pH experiments.

As a result of the tertiary and quaternary screening, the solid activity compared to the concentrates is shown in FIG. 5. Based on the results of ELISA and SRID experiment analysis for each viscous solution composition, two types of PBS solids were finally selected.

Example 5

Activity Analysis by MN Manufacturing Process

TABLE 10

| No. | Experimental group | Details |
|-----|-------------------|---------|
| 1 | Concentrate | PBS buffer |
| 2 | Solids | Polymer 1, Excipient 1 |

TABLE 10-continued

| No. | Experimental group | Details |
|-----|-------------------|---------|
| 3 | MN | MN patch packaged in aluminum bag |
| 4 | MN semi-finished product | Semi-finished product immediately after manufacturing MN patch |

The detailed composition information of the experimental group is as follows.

TABLE 11

| No. | Name | Buffer | Influenza vaccine | Influenza vaccine Concentration (mg/mL) | Polymer | Polymer concentration (W/V) | Additive 1 | Concentration of Additive 1 (W/V) | Additive 2 | Concentration of Additive 2 (W/V) |
|-----|------|--------|-------------------|------------------------------------------|---------|------------------------------|-----------|-----------------------------------|-----------|-----------------------------------|
| 1 | Concentrate, Solids, Mn, MN semi finished product | Phosphate-buffered saline (pH 7.4) | A/Michigan/45/2015 reassortant virus (H1N1) | 6.5 | carboxymethyl cellulose 250 kDa | 5% | Trehalose | 5% | Sucrose | 5% |

The results of analyzing the activity for each MN manufacturing process are shown in FIG. 5. The aforementioned standard antibody experiment and low pH experiment were performed. HA protein was coated by ½ serial dilution from the initial value of 100 ng. In FIG. 5, the Y-axis represents the last dilution value having an O.D. value higher than twice the O.D. value of the (−) control without antigen coating. Standard refers to the NIBSC standard antigen, 'concentrate' refers to concentrate, 'F2, F5' refer to solids, 'F3, F4' refer to MN and 'F6, F7' refer to MN semi-finished products. As a result, it was confirmed that the activity was not lost for each process and the values were maintained.

The composition information finally determined according to the experimental results is as follows.

According to the above experimental results, the type of buffer and the combination and concentration of additives were determined, and sodium hyaluronate 30 kD was additionally determined as the final formulation in order to select a formulation having high solubility in the skin during the process.

TABLE 12

| No. | Buffer | Influenza vaccine | Influenza vaccine hemagglutinin Concentration (mg/mL) | Polymer | Polymer concentration (w/v) | Additive 1 | Concentration of Additive 1 (w/v) | Additive 2 | Concentration of Additive 2 (w/v) |
|-----|--------|-------------------|--------------------------------------------------------|---------|------------------------------|-----------|-----------------------------------|-----------|-----------------------------------|
| 1 | Phosphate-buffered saline (pH 7.4) | reassortant virus (H1N1) | 6.5 | carboxymethyl cellulose 250 kDa | 5% | Trehalose | 5% | Sucrose | 5% |
| 2 | Phosphate-buffered saline (pH 7.4) | A/Michigan/45/2015 reassortant virus (H1N1) | 6.5 | sodium hyaluronate 30 kDa | 30% | Trehalose | 5% | Sucrose | 5% |

Example 6

Microneedle Manufacturing Method

Figure 6:
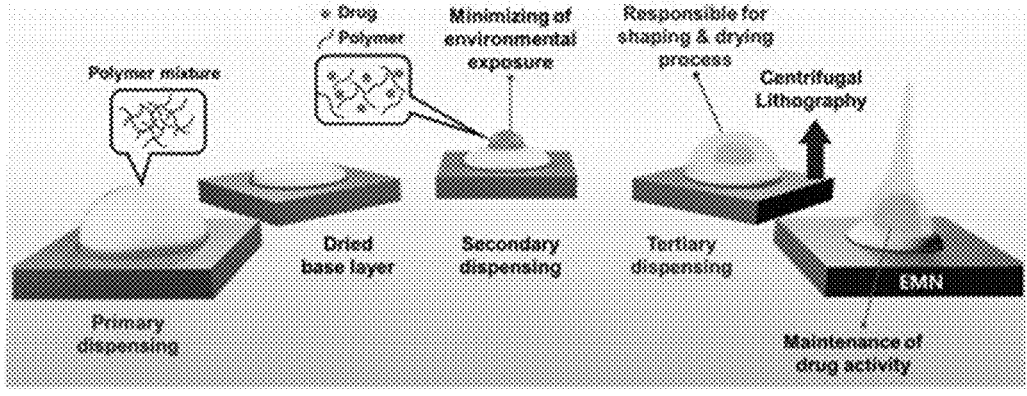
FIG. 6 shows a method for manufacturing a microneedle.

As shown in FIG. 6, the microneedle may be manufactured by including a first dispensing step of dispensing a first composition on a support; a drying step of drying the first composition to form a support part; a second dispensing step of dispensing a second composition including a drug on the support part; a third dispensing step of dispensing a third composition to cover the second composition on the support part; and a forming step of forming a middle part by the second composition and a tip part by the third composition by fluidization and centrifugal lithography.

Specifically, the first composition may include 65% (w/v) of sodium hyaluronate 30 kDa in PBS as a solvent. When the support part is formed by drying the first composition, a viscous composition (composition 2) having a composition finally containing the influenza vaccine as described in [Table 12] is applied on the support part. The third composition of sodium hyaluronate 30 kDa 65% (w/v) in PBS as a solvent may be applied to cover the second composition. Afterwards, through fluidization and centrifugal lithography steps, a middle part may be formed by the second composition and a tip part may be formed by the third composition.

The following [Table 13] shows the composition ratio based on the viscous composition, and [Table 14] shows the composition ratio based on the microneedle solid content.

TABLE 13

| Item | buffer | Hyaluronic acid | Treha-lose | Sucrose | Influenza HA | Sum |
|---|---|---|---|---|---|---|
| Mass | 1000 | 300 | 50 | 50 | 6.5 | 1406.5 |
| Ratio | 71.1% | 21.3% | 3.6% | 3.6% | 0.5% | 100.0% |

TABLE 14

| Item | Hyaluronic acid | Trehalose | Sucrose | Influenza HA | Sum |
|---|---|---|---|---|---|
| Mass | 300 | 50 | 50 | 6.5 | 406.5 |
| Ratio | 73.8% | 12.3% | 12.3% | 1.6% | 100.0% |

Example 7

Flu-DMN: Influenza Vaccine Loaded Dissolving Microneedle (DMN) Patch

Figure 7:
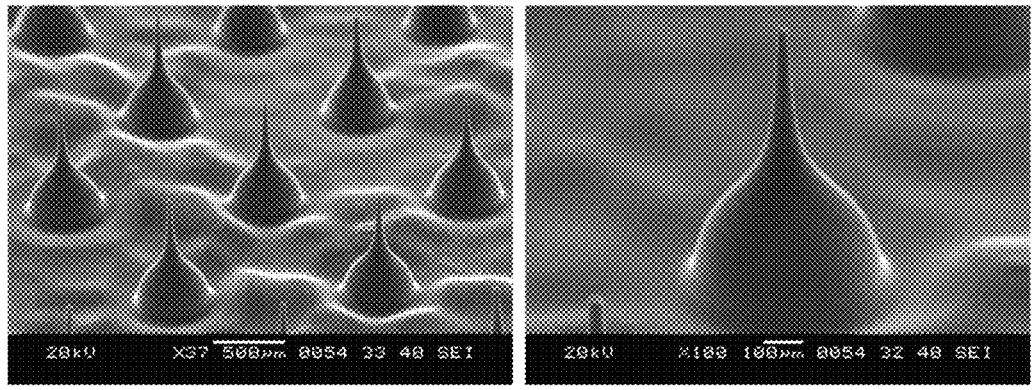
FIG. 7 shows the shape of the microneedles and how they are aligned in the patch.

The shape of the DMN is shown in FIG. 7. It can be confirmed that the DMN is aligned to the patch. 61 DMNs were aligned in an adhesive patch and attached to the skin surface for 30 minutes to deliver the influenza vaccine to a round area with a diameter of 1.5 cm. The length and diameter of the DMNs were 850±50 µm and 35±15 µm, respectively.

Figure 8:
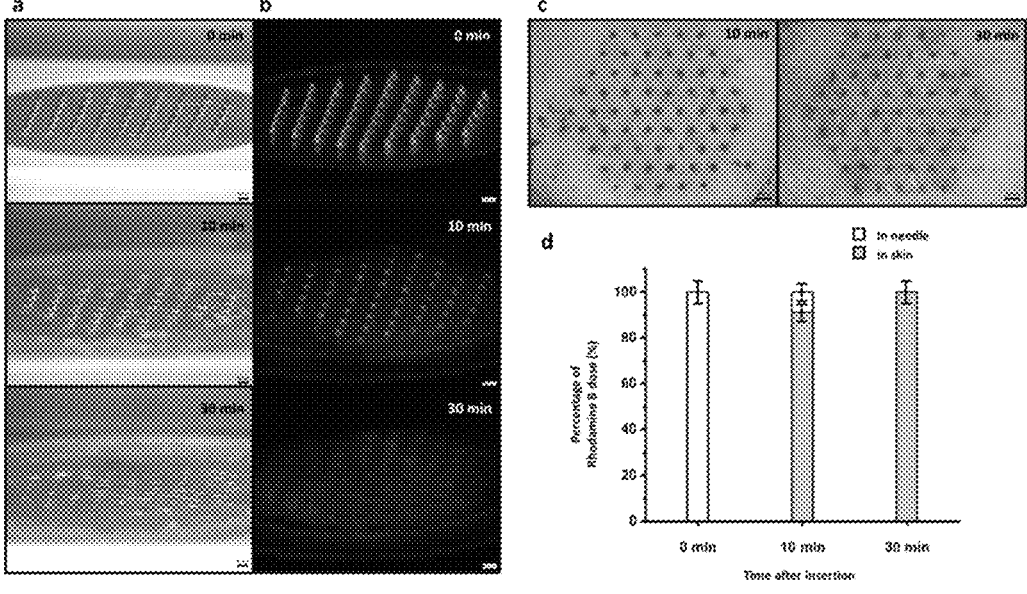
FIG. 8(a)-8(d) shows the results confirming that the influenza vaccine is dissolved and delivered to the skin.

In order to confirm that the influenza vaccine was dissolved and delivered to the skin, the influenza vaccine/fluorescent dye-attached DMN patch was applied to the pig carcass skin. As a result, it was confirmed that 91% and 99% of the fluorescent dye loaded in DMN was delivered to the skin when applied for 10 minutes and 30 minutes, respectively (FIG. 8(*a*)-8(*d*)).

The amount of influenza antigen loaded in the patch was analyzed by single radial immune diffusion (SRID). Influenza antigen was quantified as an active pharmaceutical ingredient (API) at 15 to 17 µg per patch.

The amount of influenza antigen loaded on the patch was indicated as the loading antigen, and the measured value of the antigen in the actual patch analyzed by SRID was indicated as the assay result. In addition, the ratio of the measured antigen in the patch to the antigen loaded in the patch was indicated as the activity, and as a result, 88 to 93% activity was confirmed in Microneedle Compositions 1 and 2 (FIG. 9).

Example 8

In Vivo Flu-DMN Inoculation

Mouse inoculation experiments were performed to confirm the efficacy of Flu-DMN at three different doses and with and without boosting.

Mice were divided into 8 experimental groups, 5 animals per group were targeted, and for the route of administration, intradermal administration was indicated as 'ID' and intramuscular administration was indicated as 'IM.' The presence or absence of boosting and the amount of drug were set to 5 µg, 10 µg and 15 µg. The information on the experimental groups is shown in FIG. 10.

Information on the vaccination schedule for the eight experimental groups is shown at the bottom of FIG. 10. Immediately after the start of the experiment (Day 0), animals in the 8 experimental groups were administered according to each inoculation method, and 2 weeks after the start of the experiment (2 weeks), the experimental groups for which boosting was performed were additionally administered. In order to analyze the concentration of antibodies produced in the body of the animals after inoculation of the experimental groups, eye bleeding was performed from the orbital venous plexus of the animals 2 weeks and 4 weeks after the start of the experiment (4 weeks).

Hemagglutination inhibition assay was performed to measure the antibody titer after Flu-DMN inoculation. As a result, as shown in FIG. 11, the boosted Flu-DMN showed a higher antibody titer than the positive control group without boosting, and it was confirmed that the antibody titer increased as the vaccine dose increased.

Example 9

Neutralizing Antibody Titer Measurements

The plaque reduction neutralization test (PRNT) was performed to measure neutralizing antibody titers after Flu-DMN inoculation.

As a result, as shown in FIG. 12, the boosted Flu-DMN showed a higher neutralizing antibody titer than the positive control group without boosting, and it was confirmed that the antibody titer increased as the vaccine dose increased.

Example 10

Observation of Weight Change and Survival Rate after Virus Inoculation

After performing blood collection twice, wild-type virus corresponding to twice the MLD50 (median lethal dose of mice) was inoculated into mice, and weight change and survival rate were observed for 2 weeks.

Figure 13:
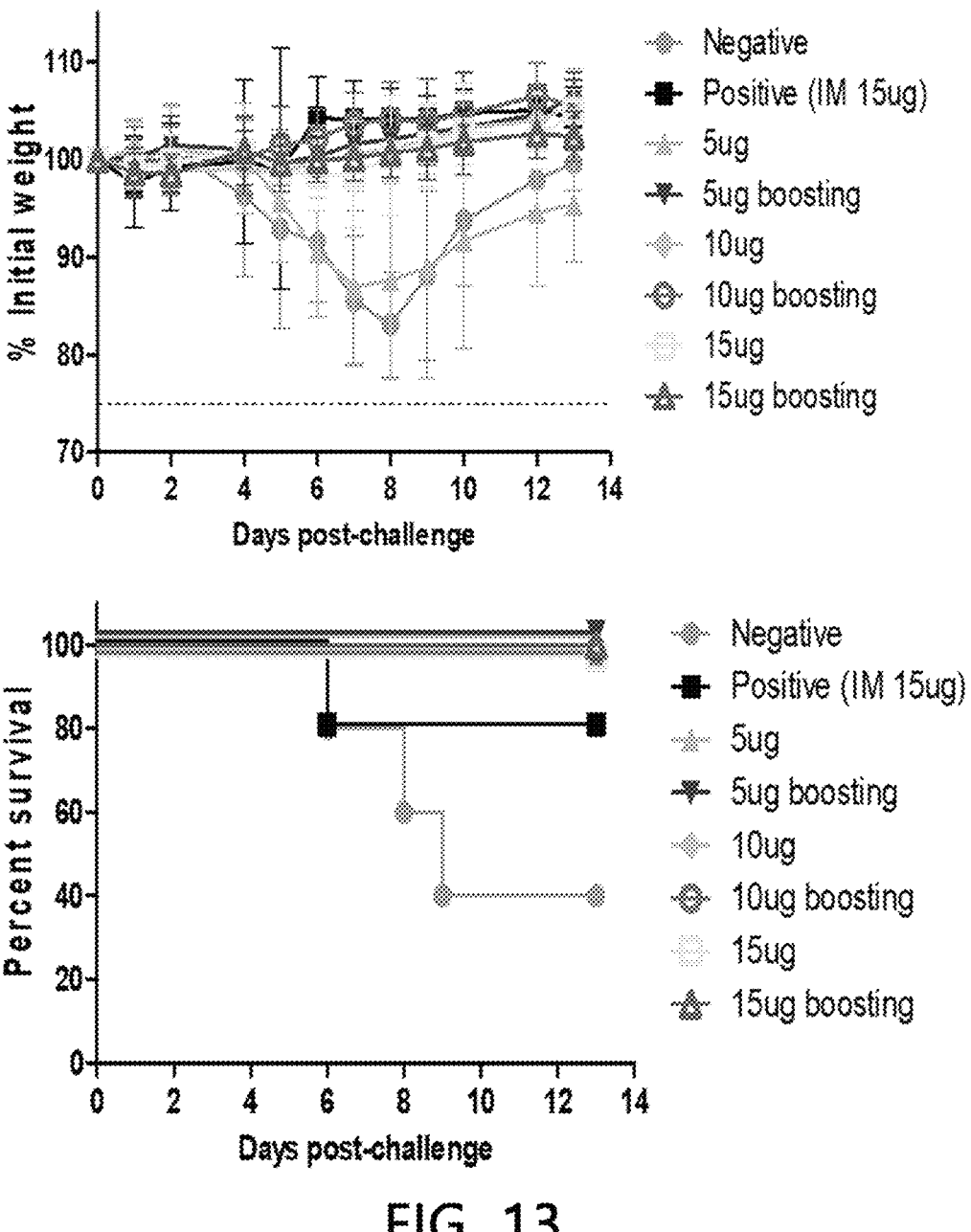
FIG. 13 shows the results of weight changes and survival rates after virus inoculation.

As a result, as shown in FIG. 13, all mice inoculated with Flu-DMN survived. On the other hand, 3 animals in the negative control group and 2 animals in the positive control group died.

As described above, specific parts of the present invention have been described in detail, and for those skilled in the art, it is clear that these specific descriptions are only preferred exemplary embodiments, and the scope of the present invention is not limited thereby. Accordingly, the substantial scope of the present invention will be defined by the appended claims and their equivalents.

EXPLANATION OF REFERENCE NUMERALS

| 10: Microneedle structure | |
| 11: Substrate layer | 12: Support part |
| 13: Interruption part | 13a: Core part |
| 14: Cover part | |
| 14a: Cover layer | 14b: Tip part |

The invention claimed is:

1. An influenza vaccine soluble microneedle composition comprising a support part, a middle part and a tip part, wherein a core part of the middle part comprises sodium hyaluronate, trehalose, sucrose and influenza vaccine, wherein the influenza vaccine soluble microneedle is manufactured by a method including a first dispensing step of dispensing a first composition comprising sodium hyaluronate and phosphate buffered saline on a support; a drying step of drying the first composition to form a support part; a second dispensing step of dispensing a second composition including phosphate buffer saline, sodium hyaluronate, trehalose, sucrose and influenza vaccine on the support part; a third dispensing step of dispensing a third composition comprising sodium hyaluronate and PBS to cover the second composition on the support part; and a forming step of forming step of forming a middle part by the second composition and a tip part by the third composition by fluidization, and and wherein the concentrations of the trehalose and sucrose are 1% to 10%, respectively in the total second composition.

2. The influenza vaccine soluble microneedle of claim 1, wherein the sodium hyaluronate is comprised at 65% (w/v) in the first composition and third composition.

3. The influenza vaccine soluble microneedle composition of claim 1, wherein the influenza vaccine is at least one selected from the group consisting of a live attenuated vaccine (LAV) or inactivated vaccine, a replicating viral vector (VVr), virus-like particles, a subunit vaccine, a non-self-replicating virus (viral vector, non-replicating), a synthetic vaccine or a genetically engineered vaccine.

4. The influenza vaccine soluble microneedle of claim 1, wherein the influenza vaccine is a polyvalent vaccine.

5. An influenza vaccine soluble microneedle array, comprising:

the influenza vaccine soluble microneedle of claim 1; and a substrate layer for supporting the microneedle.

6. The influenza vaccine soluble microneedle array of claim 5, wherein the microneedle array further comprises a microneedle comprising an immune enhancer.

7. The influenza vaccine soluble microneedle array of claim 5, wherein the microneedles are regularly arranged at regular intervals.

8. The influenza vaccine soluble microneedle array of claim 5, wherein the height of the microneedle is 500 to 1,000 μm.

9. The influenza vaccine soluble microneedle array of claim 5, wherein the microneedle is in the form of an influenza vaccine patch comprising a support on the back of the microneedle array.

10. The influenza vaccine soluble microneedle array of claim 9, wherein the vaccine patch comprises a marker formed on one side or the other side of the support to display predetermined information, and wherein the marker is formed to change color as at least one external stimulus of heat, light, moisture and pressure is applied after the microneedle is inserted into the skin.

11. The influenza vaccine soluble microneedle array of claim 10, wherein the marker is formed such that the color changes over time after the microneedle is inserted into the skin.

12. The influenza vaccine soluble microneedle array of claim 11, wherein the marker comprises a reactive material capable of undergoing an oxidation reaction, wherein the color change is made by an oxidation reaction of the reactant, and wherein the time required for the color change to be completed is formed to take 10 minutes or more.

13. The influenza vaccine soluble microneedle array of claim 10, wherein the marker includes a Quich Response (QR) code or text.

* * * * *